United States Patent
Heidner et al.

(10) Patent No.: US 9,066,826 B2
(45) Date of Patent: Jun. 30, 2015

(54) MEDICAL DEVICE DELIVERY SYSTEMS

(75) Inventors: Matthew C. Heidner, Maple Grove, MN (US); Richard C. Gunderson, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2240 days.

(21) Appl. No.: 11/100,712

(22) Filed: Apr. 7, 2005

(65) Prior Publication Data

US 2005/0228478 A1     Oct. 13, 2005

Related U.S. Application Data (63) Continuation-in-part of application No. 10/822,251, filed on Apr. 9, 2004, now abandoned.

(51) Int. Cl.

| | |
|---|---|
| *A61F 2/06* | (2013.01) |
| *A61F 11/00* | (2006.01) |
| *A61F 2/91* | (2013.01) |
| *A61F 2/95* | (2013.01) |
| A61F 2/958 | (2013.01) |
| A61F 2/966 | (2013.01) |

(52) U.S. Cl.
CPC ... *A61F 2/91* (2013.01); *A61F 2/95* (2013.01); *A61F 2002/9583* (2013.01); *A61F 2002/9665* (2013.01); *A61F 2220/0008* (2013.01); *A61F 2220/0016* (2013.01)

(58) Field of Classification Search
CPC ... A61F 2/958; A61F 2002/9511; A61F 2/95; A61F 2002/0072
USPC .................. 623/1.11, 1.12, 1.2; 606/108, 194
See application file for complete search history.

(56) References Cited

U.S. PATENT DOCUMENTS

| | | | |
|---|---|---|---|
| 4,503,569 | A | 3/1985 | Dotter |
| 4,733,665 | A | 3/1988 | Palmaz |
| 4,950,227 | A | 8/1990 | Savin et al. |
| 4,990,151 | A | 2/1991 | Wallstén |
| 5,026,377 | A | 6/1991 | Burton et al. |
| 5,290,295 | A | 3/1994 | Querals et al. |
| 5,409,495 | A | 4/1995 | Osborn |
| 5,484,444 | A | 1/1996 | Braunschweiler et al. |
| 5,534,007 | A | 7/1996 | St. Germain et al. |
| 5,645,559 | A | 7/1997 | Hachtman et al. |
| 5,693,066 | A | 12/1997 | Rupp et al. |
| 5,702,418 | A | 12/1997 | Ravenscroft |
| 5,707,376 | A | 1/1998 | Kavteladze et al. |

(Continued)

FOREIGN PATENT DOCUMENTS

| | | |
|---|---|---|
| EP | 0819411 | 1/1998 |
| EP | 1157673 | 11/2001 |

(Continued)

OTHER PUBLICATIONS

U.S. Appl. No. 08/697,453, filed Aug. 23, 1996, Louis Ellis et al.

(Continued)

*Primary Examiner* — Katherine Dowe
*Assistant Examiner* — Richard Louis
(74) *Attorney, Agent, or Firm* — Seager, Tufte & Wickhem, LLC (57) ABSTRACT

Medical device delivery systems, and related methods and components, are disclosed.

11 Claims, 6 Drawing Sheets

(56) References Cited

U.S. PATENT DOCUMENTS

| | | | |
|---|---|---|---|
| 5,709,703 A | 1/1998 | Lukie et al. | |
| 5,725,549 A | 3/1998 | Lam | |
| 5,733,325 A | 3/1998 | Robinson et al. | |
| 5,746,745 A | 5/1998 | Abele et al. | |
| 5,762,631 A | 6/1998 | Klein | |
| 5,772,669 A * | 6/1998 | Vrba | 623/1.11 |
| 5,776,142 A | 7/1998 | Gunderson | |
| 5,817,102 A | 10/1998 | Johnson et al. | |
| 5,836,965 A | 11/1998 | Jendersee et al. | |
| 5,913,871 A | 6/1999 | Werneth et al. | |
| 5,935,135 A | 8/1999 | Bramfitt et al. | |
| 5,941,908 A | 8/1999 | Goldsteen et al. | |
| 5,944,726 A | 8/1999 | Blaeser et al. | |
| 5,954,729 A | 9/1999 | Bachmann et al. | |
| 5,968,069 A | 10/1999 | Dusbabek et al. | |
| 5,976,155 A | 11/1999 | Foreman et al. | |
| 6,007,543 A | 12/1999 | Ellis et al. | |
| 6,007,545 A | 12/1999 | Venturelli | |
| 6,027,510 A | 2/2000 | Alt | |
| 6,051,001 A | 4/2000 | Borghi | |
| 6,053,943 A | 4/2000 | Edwin et al. | |
| 6,066,169 A | 5/2000 | McGuinness | |
| 6,077,273 A | 6/2000 | Euteneuer et al. | |
| 6,077,295 A | 6/2000 | Limon et al. | |
| 6,077,297 A * | 6/2000 | Robinson et al. | 623/1.11 |
| 6,106,530 A | 8/2000 | Harada | |
| 6,110,180 A | 8/2000 | Foreman et al. | |
| 6,120,522 A | 9/2000 | Vrba et al. | |
| 6,123,712 A | 9/2000 | Di Caprio et al. | |
| 6,126,685 A | 10/2000 | Lenker et al. | |
| 6,149,996 A | 11/2000 | Helgerson et al. | |
| 6,159,227 A | 12/2000 | Di Caprio et al. | |
| 6,168,616 B1 | 1/2001 | Brown, III | |
| 6,168,617 B1 | 1/2001 | Blaeser et al. | |
| 6,203,558 B1 | 3/2001 | Dusbabek et al. | |
| 6,214,036 B1 | 4/2001 | Letendre et al. | |
| 6,228,110 B1 | 5/2001 | Munsinger | |
| 6,241,738 B1 * | 6/2001 | Dereume | 606/108 |
| 6,254,632 B1 | 7/2001 | Wu et al. | |
| 6,258,099 B1 | 7/2001 | Mareiro et al. | |
| 6,264,683 B1 | 7/2001 | Stack et al. | |
| 6,280,412 B1 | 8/2001 | Pederson et al. | |
| 6,296,660 B1 | 10/2001 | Roberts et al. | |
| 6,302,906 B1 | 10/2001 | Goicoechea et al. | |
| 6,309,402 B1 | 10/2001 | Jendersee et al. | |
| 6,322,586 B1 | 11/2001 | Monroe et al. | |
| 6,325,814 B1 | 12/2001 | Euteneuer et al. | |
| 6,331,188 B1 | 12/2001 | Lau et al. | |
| 6,350,277 B1 | 2/2002 | Kocur | |
| 6,371,962 B1 | 4/2002 | Ellis et al. | |
| 6,375,676 B1 | 4/2002 | Cox | |
| 6,380,457 B1 | 4/2002 | Yurek et al. | |
| 6,391,032 B2 | 5/2002 | Blaeser et al. | |
| 6,391,050 B1 | 5/2002 | Broome | |
| 6,391,051 B2 | 5/2002 | Sullivan et al. | |
| 6,395,008 B1 | 5/2002 | Ellis et al. | |
| 6,395,017 B1 | 5/2002 | Dwyer et al. | |
| 6,419,685 B2 | 7/2002 | Di Caprio et al. | |
| 6,428,566 B1 | 8/2002 | Holt | |
| 6,443,979 B1 | 9/2002 | Stalker et al. | |
| 6,468,298 B1 | 10/2002 | Pelton | |
| 6,468,299 B2 | 10/2002 | Stack et al. | |
| 6,494,906 B1 | 12/2002 | Owens | |
| 6,506,201 B2 | 1/2003 | Di Caprio et al. | |
| 6,517,547 B1 | 2/2003 | Feeser et al. | |
| 6,517,570 B1 | 2/2003 | Lau et al. | |
| 6,569,192 B1 | 5/2003 | Foreman et al. | |
| 6,582,460 B1 * | 6/2003 | Cryer | 623/1.11 |
| 6,607,551 B1 | 8/2003 | Sullivan et al. | |
| 6,620,191 B1 | 9/2003 | Svensson | |
| 6,623,518 B2 | 9/2003 | Thompson et al. | |
| 6,660,031 B2 | 12/2003 | Tran et al. | |
| 6,676,667 B2 | 1/2004 | Mareiro et al. | |
| 6,682,553 B1 | 1/2004 | Webler, Jr. | |
| 6,776,791 B1 * | 8/2004 | Stallings et al. | 623/1.11 |
| 6,814,746 B2 * | 11/2004 | Thompson et al. | 623/1.11 |
| 6,837,901 B2 * | 1/2005 | Rabkin et al. | 623/1.11 |
| 6,858,034 B1 * | 2/2005 | Hijlkema et al. | 606/108 |
| 6,890,337 B2 | 5/2005 | Feeser et al. | |
| 6,896,180 B2 | 5/2005 | Miodunski et al. | |
| 6,960,227 B2 | 11/2005 | Jones et al. | |
| 7,001,422 B2 | 2/2006 | Escamilla et al. | |
| 7,152,605 B2 | 12/2006 | Khairkhahan et al. | |
| 2001/0007082 A1 | 7/2001 | Dusbabek et al. | |
| 2002/0049466 A1 | 4/2002 | Euteneuer et al. | |
| 2002/0055767 A1 | 5/2002 | Forde et al. | |
| 2002/0095204 A1 | 7/2002 | Thompson et al. | |
| 2002/0099435 A1 | 7/2002 | Stinson | |
| 2002/0120321 A1 | 8/2002 | Gunderson et al. | |
| 2002/0120322 A1 | 8/2002 | Thompson et al. | |
| 2002/0120323 A1 | 8/2002 | Thompson et al. | |
| 2002/0123794 A1 | 9/2002 | Ellis et al. | |
| 2002/0138081 A1 | 9/2002 | Blaeser et al. | |
| 2002/0144757 A1 | 10/2002 | Craig et al. | |
| 2002/0151955 A1 | 10/2002 | Tran et al. | |
| 2002/0156519 A1 | 10/2002 | Di Caprio et al. | |
| 2003/0018380 A1 | 1/2003 | Craig et al. | |
| 2003/0077200 A1 | 4/2003 | Craig et al. | |
| 2003/0114912 A1 | 6/2003 | Sequin et al. | |
| 2003/0212451 A1 | 11/2003 | Cox et al. | |
| 2004/0084523 A1 | 5/2004 | Miodunski et al. | |
| 2004/0148008 A1 * | 7/2004 | Goodson et al. | 623/1.12 |
| 2004/0204749 A1 | 10/2004 | Gunderson | |
| 2005/0131514 A1 * | 6/2005 | Hijlkema et al. | 623/1.12 |
| 2005/0165439 A1 * | 7/2005 | Weber et al. | 606/191 |

FOREIGN PATENT DOCUMENTS

| | | |
|---|---|---|
| EP | 1369098 | 10/2003 |
| WO | 93/22986 | 11/1993 |
| WO | 94/15549 | 7/1994 |
| WO | 98/07390 | 2/1998 |
| WO | WO 00/71058 | 11/2000 |
| WO | 02/32496 | 4/2002 |
| WO | WO 02/41805 | 5/2002 |
| WO | 02/47582 | 6/2002 |

OTHER PUBLICATIONS

International Search Report, PCT/US2004/011023, Oct. 11, 2004.
Schetsky, L., "Shape Memory Alloys", Encyclopedia of Chemical Technology (3rd ed.), John Wiley & Sons, 1982, vol. 20, pp. 726-736.
International Application No. PCT/US2005/011752 Search Report, dated Aug. 26, 2005.

* cited by examiner

MEDICAL DEVICE DELIVERY SYSTEMS

CROSS-REFERENCE TO RELATED APPLICATIONS

This application is a continuation-in-part of, and claims priority under 35 U.S.C. §120 to, commonly owned U.S. patent application Ser. No. 10/822,251, filed on Apr. 9, 2004, now abandoned and entitled "Medical Device Delivery Systems", the entire contents of which are herein incorporated by reference.

TECHNICAL FIELD

This invention relates to medical device delivery systems, and related methods and components.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include a sheath surrounding a catheter with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen. In many instances, a bumper can be included in the system to, for example, aid in deployment of the stent from the system.

SUMMARY

The invention relates to medical device delivery systems, and related methods and components.

In general, the invention relates to implantable medical endoprosthesis delivery systems (e.g., stent delivery systems), as well as related components and methods. The systems can be used, for example, to deliver a medical endoprosthesis (e.g., a stent) to a desired location within a lumen of a subject (e.g., an artery of a human).

In some embodiments, the inner member has a portion that extends outwardly (e.g., a retainer) so that it can be partially disposed over the implantable medical endoprosthesis and so that it can interdigitate with the implantable medical endoprosthesis.

In certain embodiments, the outer member has a portion that extends inwardly (e.g., a retainer) so that it can interdigitate with the implantable medical endoprosthesis.

In some embodiments, methods can include at least partially disposing a medical endoprosthesis (e.g., a stent) within a lumen of a subject (e.g., an artery of a human). The methods can include moving the outer member proximally (e.g., so that the implantable medical endoprosthesis is released and can engage a wall of the lumen).

In certain embodiments, an implantable medical endoprosthesis delivery system can exhibit relatively high accuracy in positioning an implantable medical endoprosthesis, and/or increased control over the deployment of an implantable medical endoprosthesis.

In some embodiments, a portion of a medical endoprosthesis delivery system that interdigitates with an implantable medical endoprosthesis delivery system can provide an operator of an implantable medical endoprosthesis delivery system with information about the location of the implantable medical endoprosthesis within the system. As an example, one or more radiopaque materials and/or one or more MRI-visible materials can be used to form the portion of the medical endoprosthesis delivery system that interdigitates with the implantable medical endoprosthesis delivery system.

Features and advantages of the invention are in the description, drawings, and claims.

DETAILED DESCRIPTION

Figure 1:
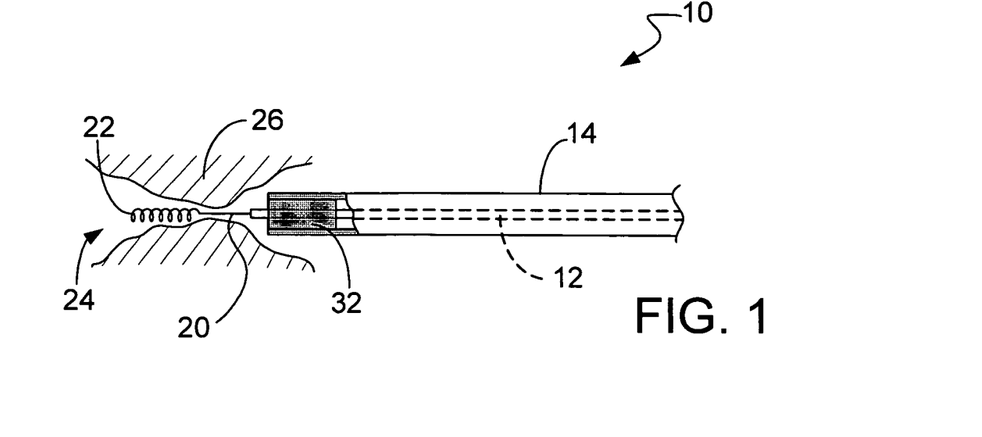
FIGS. 1-3 are side views of a distal portion of an embodiment of an implantable medical endoprosthesis delivery system at different stages of delivery of the implantable medical endoprosthesis.
Figure 2:
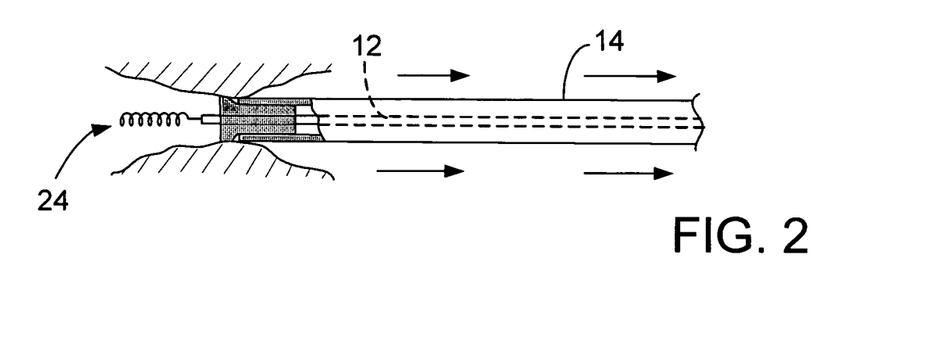
Figure 3:
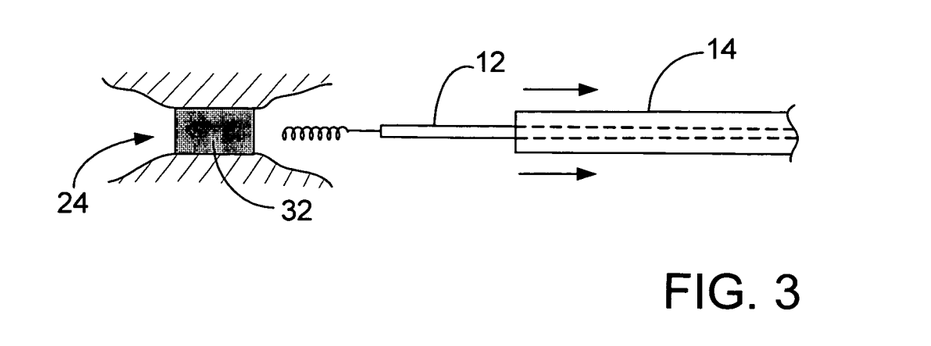

FIGS. 1-3 show a distal end of an implantable medical endoprosthesis delivery system 10 that includes an inner member 12, an outer member 14 surrounding inner member 12, and a stent 32 positioned between inner member 12 and outer member 14. The distal end of system 10 is dimensioned for insertion into a body lumen (e.g., an artery of a human). A guide wire 20 with a blunted end 22 is inserted into a body lumen 24 by, for example, making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, inner member 12, stent 32 and outer member 14 are placed over the proximal end of guide wire 20. Inner member 12, stent 32 and outer member 14 are moved distally over guide wire 20 and positioned within lumen 24 so that stent 32 is adjacent constricted site 26 of lumen 24. Outer member 14 is moved proximally, allowing stent 32 to expand and engage constricted site 26. Outer member 14, inner member 12 and guide wire 20 are removed from body lumen 24, leaving stent 32 engaged with constricted site 26.

Figure 4:
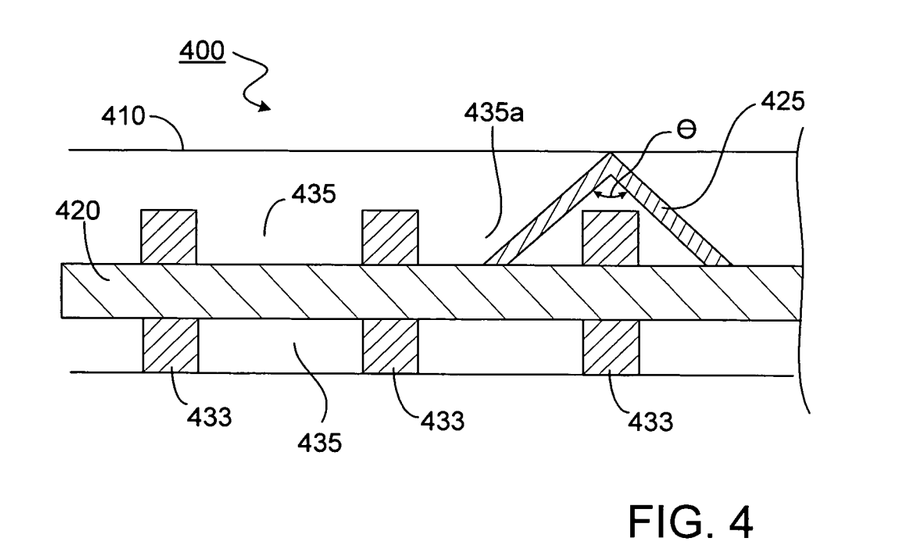
FIGS. 4-7 are side views of a distal portion of an embodiment of an implantable medical endoprosthesis delivery system at different stages of delivery of the implantable medical endoprosthesis.

FIG. 4 shows a stent delivery system 400 that includes an outer member 410, an inner member 420 and a stent having struts 433 and openings 435 between struts 433. Inner member 420 includes a retainer 425 disposed around the outer circumference of inner member 420. Retainer 425 is partially disposed over the stent and interdigitated with an opening 435a in the stent. As explained below with reference to FIGS. 5-7, system 400 can be used to deliver the stent with enhanced accuracy and/or control.

Figure 5:
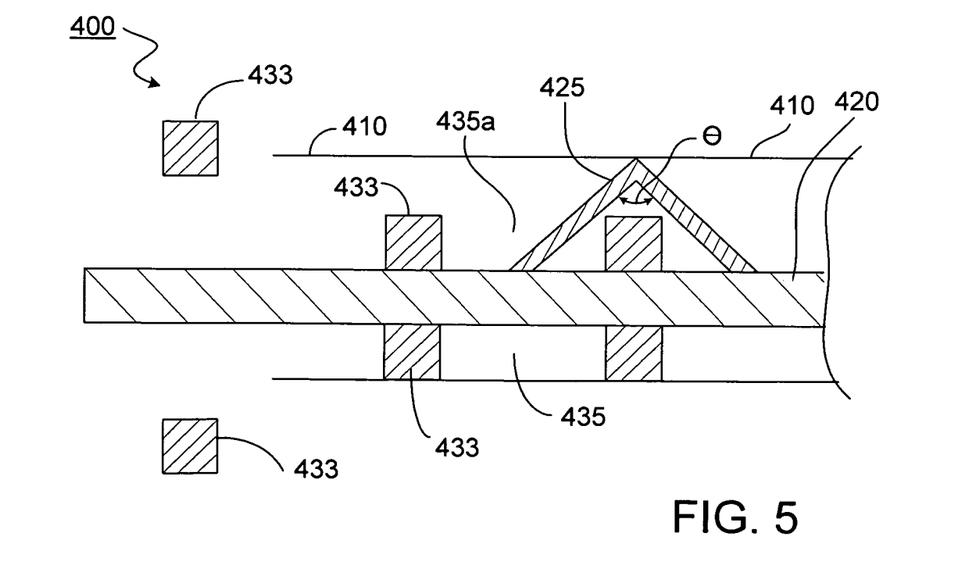
Figure 6:
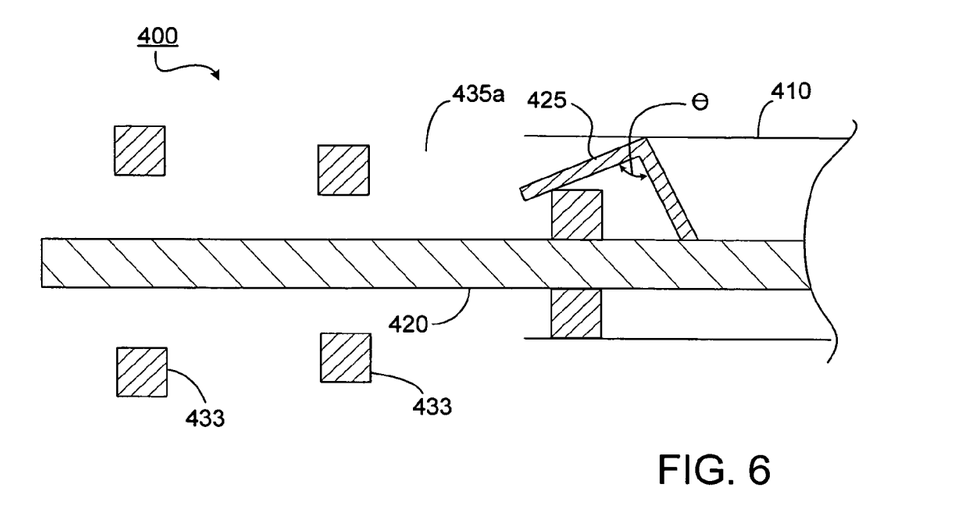
Figure 7:
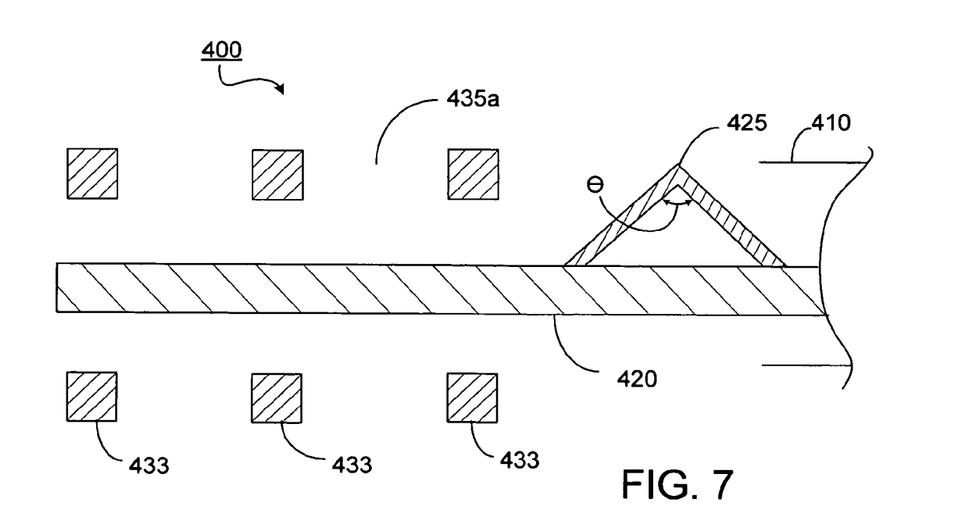

In FIG. 5, outer member 410 has moved proximally an amount sufficient to release a distal portion of the stent, but retainer 425 remains partially disposed over the stent and interdigitated with opening 435a in the stent. In FIG. 6, outer member 410 has moved proximally an amount sufficient to release almost all of the stent. Retainer 425 is no longer interdigitated with opening 435a, but retainer 425 remains partially disposed over the stent. In FIG. 7, outer member 410 has moved proximally of the proximal end of the stent, and the stent is fully released. As shown in FIGS. 5-7, during the stages in the release of the stent, the stent remains substantially unmoved with respect to the distal direction.

In certain embodiments, retainer 425 is designed so that the angle, Θ, remains substantially unchanged during release of the stent. This can reduce the amount of potential energy that becomes stored in retainer 425 during the stages in the release of the stent, which can enhance the ability to control the positioning of the stent during its release. In some embodiments, the angle, Θ, remains can change during release of the stent (e.g., one or more portions of retainer 425 can distort during release of the stent).

Although shown as being triangular, more generally, retainer 425 can have any desired shape. Examples of shapes that retainer 425 can include U-shaped, square shaped, rectangular shaped and semi-circular shaped.

In general, retainer 425 is formed of a material that is rigid enough for retainer 425 to substantially prevent the stent from moving distally while retainer 425 is interdigitated with the stent, but that is flexible enough to pivot and allow the full release of the stent as outer member 410 is moved proximally over the proximal end of the stent. Examples of materials from which retainer 425 can be formed include polymers, metals, alloys, ceramics and fiber reinforced composites.

Examples of polymers include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyolefins (e.g., Marlex® polyethylene, Marlex® polypropylene), high-density polyethylene (HDPE), low-density polyethylene (LDPE), polyamides (e.g., nylons, Vestamid®), polyimides, and combinations of these materials. In certain embodiments (e.g., when it is desirable to reduce the force used to retract outer member 410), retainer 425 can be made of a material having a relatively low coefficient of friction (e.g., a fluoropolymer or a silicone). Examples of fluoropolymers include PTFE and FEP. Alternatively or additionally, retainer 425 can be made of a material that includes a lubricious additive (e.g., a fluoropolymer, a silicone, an ultrahigh molecular weight polyethylene, an oil, or blends thereof).

Examples of metals and alloys include stainless steel, platinum, gold, tantalum, MP35N (a nickel-cobalt-chromium-molybdenum alloy), nickel-titanium alloys (e.g., FLEXINOL®, manufactured by Dynalloy, Inc. of Costa Mesa, Calif.) and shape-memory materials. Examples of shape memory materials include metal alloys, such as nitinol (e.g., 55% nickel, 45% titanium), silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium (Fe3Be), iron platinum (Fe3Pt), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). See, e.g., Schetsky, L. McDonald, "Shape Memory Alloys", Encyclopedia of Chemical Technology (3rd ed.), John Wiley & Sons, 1982, vol. 20. pp. 726-736.

In some embodiments, retainer 425 can be entirely or partially formed of one or more radiopaque materials (e.g., to enhance the visibility of retainer 425 during X-ray fluoroscopy). Certain radiopaque materials (e.g., platinum, gold, tantalum) are noted above. Additional radiopaque materials include platinum enriched stainless steels, such as disclosed in published U.S. patent applications US-2003-0018380-A1, 2002-0144757-A1, and 2003-0077200-A1, all of which are hereby incorporated by reference. In certain embodiments in which retainer 425 is partially formed of a radiopaque material, retainer 425 is formed of a polymer having the radiopaque material(s) disposed therein.

In some embodiments, retainer 425 can be entirely or partially formed of one or more MRI-visible materials. As used herein, a MRI-visible material refers to a material that has a magnetic susceptibility of at most about one or less (e.g., at most about 0.5 or less; at most about zero or less) when measured at 25° C. An MRI-visible material can be, for example, a non-ferrous metal-alloy containing paramagnetic elements (e.g., dysprosium or gadolinium) such as terbium-dysprosium, dysprosium, and gadolinium; a non-ferrous metallic band coated with an oxide or a carbide layer of dysprosium or gadolinium (e.g., $Dy_2O_3$ or $Gd_2O_3$); a non-ferrous metal (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; or nanocrystalline particles of the transition metal oxides (e.g., oxides of Fe, Co, Ni).

In general, retainer 425 can be integral with inner member 420 or retainer can be a separate element that is attached to inner member 420. In embodiments in which retainer 425 is integral with inner member 420, retainer 425 can be formed, for example, by molding (e.g., extrusion molding, blow molding, injection molding, insert molding), and/or using material removal methods (e.g., lapping, laser removal, water jet removal). In embodiments in which retainer 425 is attached to inner member 420, retainer 425 and inner member 420 are generally formed separately and subsequently attached, such as, for example, using RF heating, laser bonding, microwave heating, and/or an adhesive. Examples of adhesives include epoxy adhesives, UV curable adhesives and cyanoacrylate adhesive (e.g., medical grade cyanoacrylate adhesives). Commercially available adhesives include epoxy adhesives available from HB Fuller (e.g., HB Fuller 3507 epoxy adhesive, HB Fuller 2139 epoxy adhesive) and the Loctite® brand products available from Henkel Technologies (e.g., Assure™ 425 Surface Curing Threadlocker).

In general, the stent is a self-expanding stent. Examples of materials from which the stent include shape memory materials, such those disclosed above regarding retainer 425.

Inner member 410 and outer member 420 are generally made of polymeric materials, such as those disclosed above regarding retainer 425.

Figure 8:
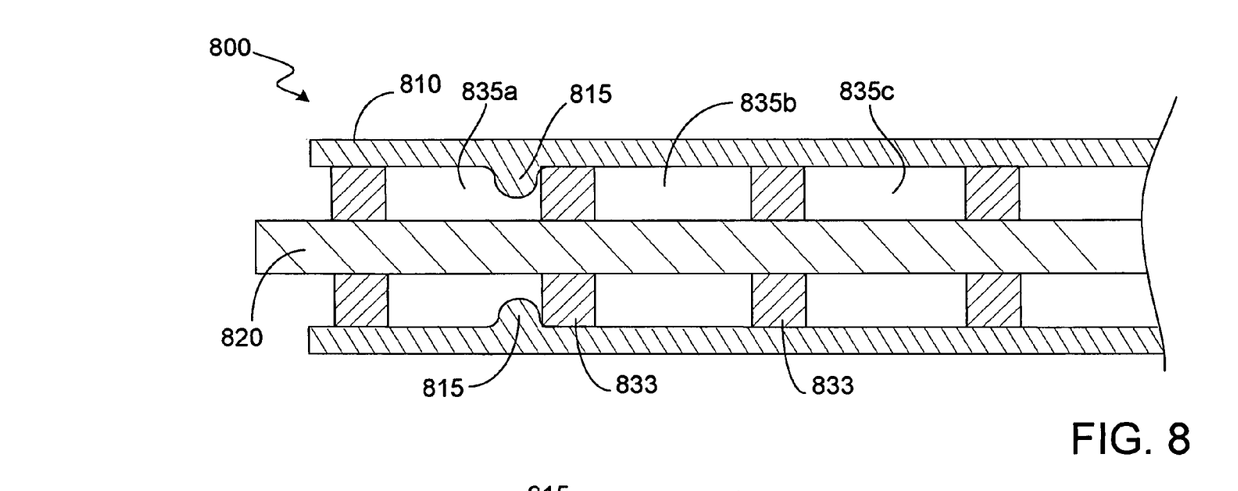
FIGS. 8-12 are side views of a distal portion of an embodiment of an implantable medical endoprosthesis delivery system at different stages of delivery of the implantable medical endoprosthesis.

While embodiments have been described in which an inner member has a retainer, in some embodiments, an outer member can have a retainer. For example, FIG. 8 shows a stent delivery system 800 that includes an outer member 810, an inner member 820 and a stent having struts 833 and openings 835 between openings 835. Outer member 810 includes a retainer 815 disposed around the inner circumference of outer member 810. Retainer 815 is interdigitated with an opening 835a in the stent. As explained below with reference to FIGS. 9-12, system 800 can be used to deliver the stent with enhanced accuracy and/or control.

Figure 9:
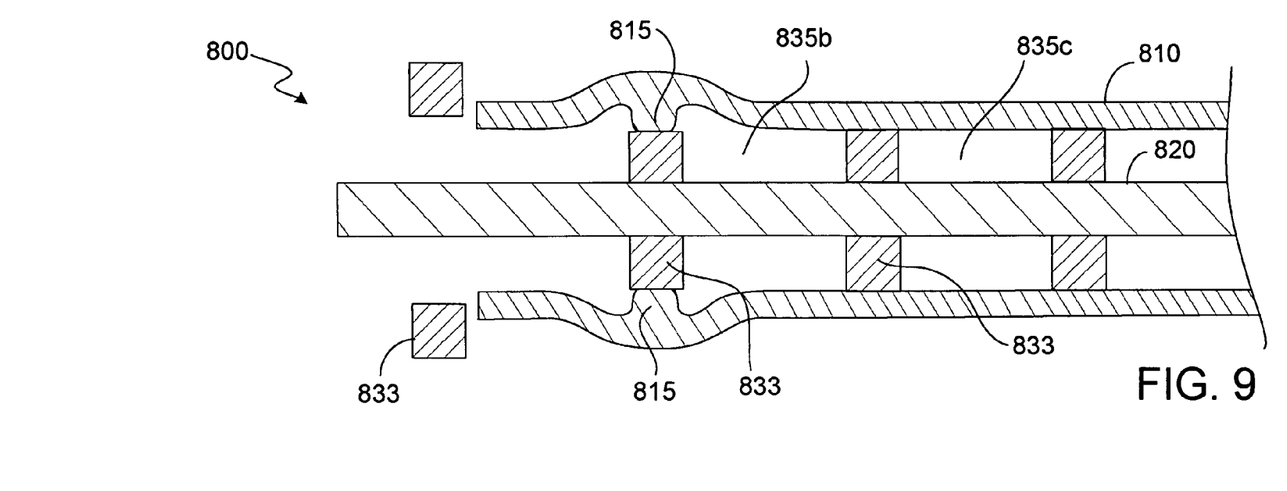
Figure 10:
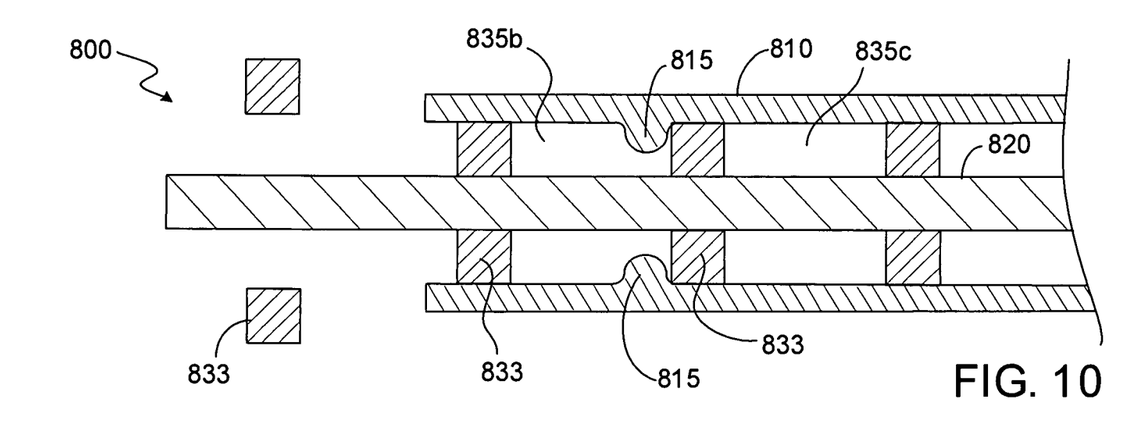
Figure 11:
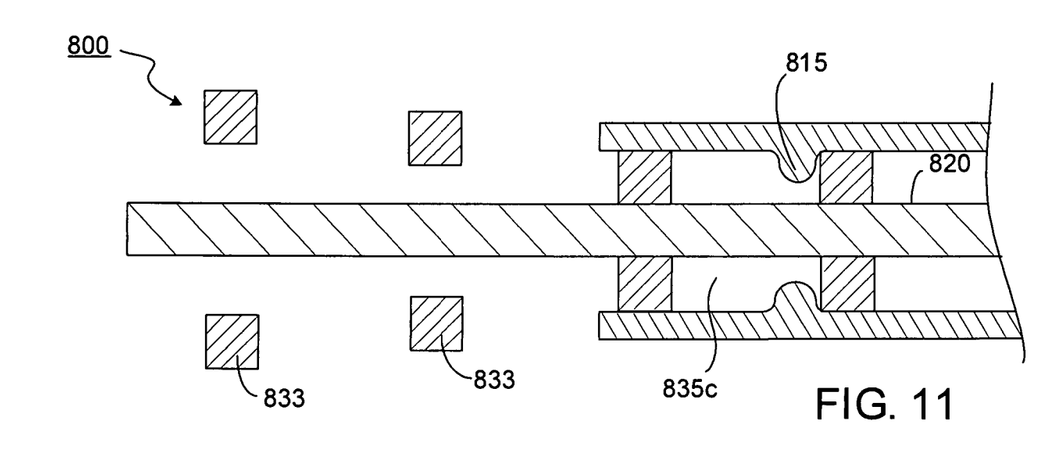
Figure 12:
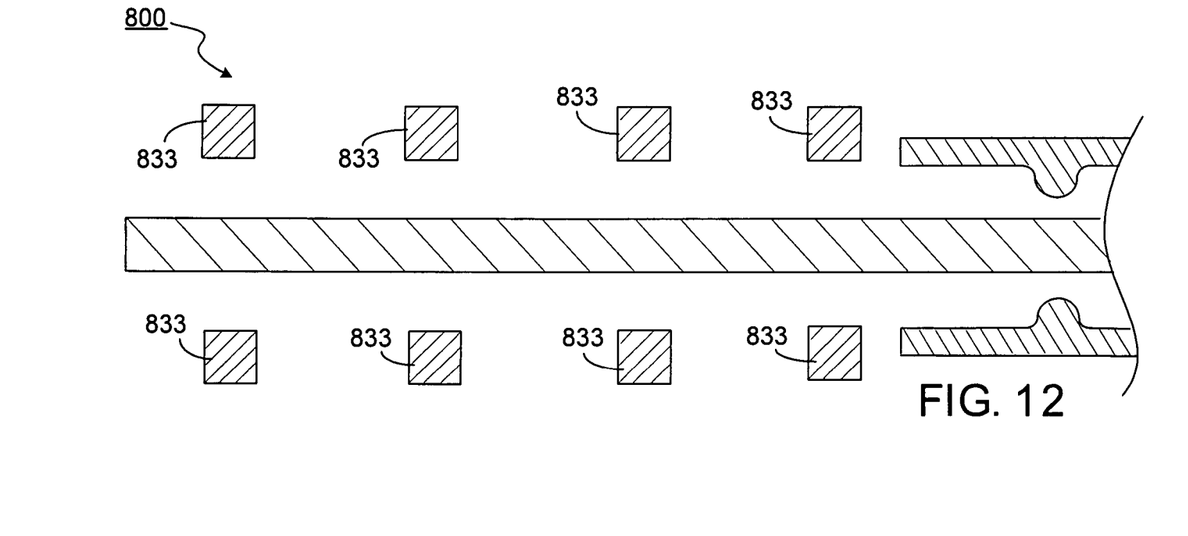

In FIG. 9, outer member 810 has moved proximally so that a portion of outer member 810 is distorted outwardly and so that retainer 815 is on a strut 833. In FIG. 10, outer member 810 has moved proximally an amount sufficient to release a distal portion of the stent, but retainer 815 has also moved proximally and is now interdigitated with an opening 835b (located proximally of opening 835a) of the stent. In FIG. 11, outer member 810 has moved proximally an amount sufficient to release most of the stent, but retainer 815 has also moved more proximally and is now interdigitated with an opening 835c (located proximally of opening 835a and 835b)

of the stent. In FIG. 12, outer member 810 has moved proximally of the proximal end of the stent, and the stent is fully released. As shown in FIGS. 9-12, during the stages in the release of the stent, the stent remains substantially unmoved with respect to the distal direction.

Generally, retainer 815 is designed so that it can move relatively smooth over the stent as outer member 810 is moved proximally. This can reduce the amount of potential energy that becomes stored in retainer 815 during the stages in the release of the stent, which can enhance the ability to control the positioning of the stent during its release.

In general, retainer 815 can be formed of one or more of the materials disclosed above regarding retainer 425.

Generally, retainer 815 can be integral with outer member 810 or retainer can be a separate element that is attached to outer member 810. In general, retainer 815 can be formed using the methods disclosed above regarding retainer 425.

While certain embodiments of an outer member having a retainer have been described, other embodiments are possible. As an example, the retainer could be formed of an inflatable member (e.g., an inflatable balloon) that extends inwardly from the outer member. The size and shape of the inflatable member could be manipulated by inflating or deflating the inflatable member. As an example, the inflatable member could be configured so that, the inflatable member extends inwardly from the outer member and acts as a retainer when inflated, but extends inwardly little if any distance and does not act as a retainer when deflated. As another example, the inflatable member could be configured to interdigitate with multiple struts of a stent when inflated, and interdigitate with fewer (e.g., none) of the struts when deflated.

While certain embodiments have been described, other embodiments are possible.

As an example, while embodiments have been described in which a retainer is disposed around the outer circumference of an inner member, in some embodiments a retainer can be disposed around only a portion of the outer circumference of the inner member.

As another example, while embodiments have been described in which a retainer is disposed around the inner circumference of an outer member, in some embodiments a retainer can be disposed around only a portion of the inner circumference of the outer member.

As a further example, in some embodiments, an inner member can include multiple retainers. The retainers can be positioned radially around the inner member (e.g., at substantially the same distance longitudinally along the inner member), and/or the retainers can be positioned at different distances longitudinally along the inner member.

As another example, while embodiments have been described in which an outer member includes a single retainer, in some embodiments, an outer member can include multiple retainers. The retainers can be positioned radially around the outer member (e.g., at substantially the same distance longitudinally along the outer member), and/or the retainers can be positioned at different distances longitudinally along the outer member.

As a further example, while embodiments have been described in which an inner member has one or more retainers or an outer member has one or more retainers, in some embodiments, each of the inner and outer members can have one or more retainers.

As an additional example, while the retention of self-expanding stents has been described, other types of implantable medical endoprostheses are capable of being retained by a retainer. Examples of implantable medical endoprostheses include balloon-expandable stents, stent-grafts and vena cava filters.

As another example, in some embodiments, a retainer (e.g., a retainer on an inner member, a retainer on an outer member) can be formed of a material that changes shape so that, without moving the inner or outer members, the retainer is interdigitated with the stent when the retainer has one shape, and the retainer is not interdigitated with the stent when the retainer has another shape. For example, the retainer can be formed of an electroactive polymer that changes shape when a current is applied to the material. In such embodiments, the retainer could be configured to interdigitate with the stent when an electric current is not applied to the material, and the retainer could be configured to not interdigitate with the stent when a current is applied to the material, or vice-versa.

Other embodiments are in the claims.

What is claimed is:

1. A medical endoprosthesis delivery system, comprising: an inner member having an outwardly extending portion, wherein the inner member is a single body; an outer member at least partially surrounding the inner member, the inner and the outer members being configured so that an implantable medical endoprosthesis can be disposed between the inner and outer members; an implantable medical endoprosthesis disposed between the inner member and the outer member; wherein the outwardly extending portion includes a proximal end that is disposed proximal of a proximal end of the implantable medical endoprosthesis; wherein the outwardly extending portion includes a distal end that is disposed proximal of a distal end of the inner member, and wherein the distal end of the outwardly extending portion interdigitates with an opening in the implantable medical endoprosthesis; wherein the outwardly extending portion includes an angled region that is disposed over the implantable medical endoprosthesis and that is positioned between the proximal end and the distal end of the outwardly extending portion; wherein the angled portion forms an angle that remains substantially constant during deployment of the implantable medical endoprosthesis; and wherein the outward extending portion is configured to pivot relative to the inner member during deployment of the medical endoprosthesis between a first configuration where the distal end of the outwardly extending portion contacts the inner member and a second configuration; wherein the outwardly extending portion is biased to pivot the distal end of the outwardly extending portion radially inward toward the first configuration.

2. The medical endoprosthesis delivery system of claim 1, wherein the outwardly extending portion of the inner member is configured so that, when the implantable medical endoprosthesis is disposed between the inner and outer members, the outwardly extending portion of the inner member substantially prevents the implantable medical endoprosthesis from moving distally with respect to the inner member.

3. The medical endoprosthesis delivery system of claim 1, wherein the outwardly extending portion of the inner member is configured so that, when the implantable medical endoprosthesis is disposed between the inner and outer members and the outer member is moved proximally over a distal portion of the implantable medical endoprosthesis, the outwardly extending portion of the inner member substantially prevents the implantable medical endoprosthesis from moving distally with respect to the inner member.

4. A method of treating a lumen within a subject, the method comprising:
at least partially inserting the system of claim 1 into the lumen.

5. The method of claim 4, further comprising moving the outer member proximally.

6. A medical endoprosthesis delivery system, comprising:
an inner member, the inner member having an outer surface with a maximum outer diameter;
an outer member at least partially surrounding the inner member;
an implantable medical endoprosthesis disposed between the inner and outer members;
a retainer attached to the inner member and being configured to pivot relative to the inner member, wherein the retainer is configured so that when the implantable medical endoprosthesis is disposed between the inner and outer members, the retainer includes an angled portion that is at least partially disposed over the implantable medical endoprosthesis and a distal end that interdigitates with an opening of the implantable medical endoprosthesis;
wherein the retainer includes a distal portion and a proximal portion and wherein the length of the distal portion is approximately equal to the length of the proximal portion;
wherein the angled portion of the retainer is oriented at a constant angle during deployment of the implantable medical endoprosthesis;
wherein the implantable medical endoprosthesis is configured to shift between an expanded configuration and a collapsed configuration; and
wherein when the implantable medical endoprosthesis is in the collapsed configuration, the implantable medical endoprosthesis has a maximum outer diameter that is greater than the maximum outer diameter of the inner member;
wherein the retainer is biased to pivot the distal end of the retainer radially inward toward the inner member between a first configuration where the distal end contacts the inner member and a second configuration.

7. The medical endoprosthesis delivery system of claim 6, wherein the inner member is a single body.

8. A medical endoprosthesis delivery system, comprising:
an inner member;
an outer member at least partially surrounding the inner member;
an implantable medical endoprosthesis disposed between the inner and outer members;
a pivoting retainer attached to the inner member, wherein the retainer is configured so that when the implantable medical endoprosthesis is disposed between the inner and outer members, the retainer can be at least partially disposed over the implantable medical endoprosthesis and can interdigitate with an opening of the implantable medical endoprosthesis;
wherein a distal end of the pivoting retainer is disposed proximal of a distal end of the inner member; and
wherein the pivoting retainer is biased to pivot the distal end of the pivoting retainer radially inward toward the inner member between a first configuration where the distal end contacts the inner member and a second configuration.

9. The medical endoprosthesis delivery system of claim 8, wherein the inner member is a single body.

10. The medical endoprosthesis delivery system of claim 1, wherein the outwardly extending portion is formed integrally with the inner member.

11. The medical endoprosthesis delivery system of claim 6, wherein the retainer is formed integrally with the inner member.

* * * * *